United States Patent
Osadchy et al.

(10) Patent No.: US 8,400,164 B2
(45) Date of Patent: Mar. 19, 2013

(54) CALIBRATION AND COMPENSATION FOR ERRORS IN POSITION MEASUREMENT

(75) Inventors: Daniel Osadchy, Haifa (IL); Meir Bar-Tal, Zichron Ya'acov (IL)

(73) Assignee: Biosense Webster, Inc., Diamond Bar, CA (US)

( * ) Notice: Subject to any disclaimer, the term of this patent is extended or adjusted under 35 U.S.C. 154(b) by 419 days.

(21) Appl. No.: 12/611,500

(22) Filed: Nov. 3, 2009

(65) Prior Publication Data

US 2010/0117659 A1    May 13, 2010

Related U.S. Application Data

(60) Provisional application No. 61/113,722, filed on Nov. 12, 2008.

(51) Int. Cl.
*G01R 35/00* (2006.01)
*A61B 5/05* (2006.01)

(52) U.S. Cl. .................................. 324/601; 600/424

(58) Field of Classification Search ............. 324/601, 324/713, 522; 600/424
See application file for complete search history.

(56) References Cited

U.S. PATENT DOCUMENTS

| | | | |
|---|---|---|---|
| 5,983,126 A | 11/1999 | Wittkampf | |
| 6,226,542 B1 | 5/2001 | Reisfeld | |
| 6,233,476 B1 * | 5/2001 | Strommer et al. | 600/424 |
| 6,301,496 B1 | 10/2001 | Reisfeld | |
| 6,814,733 B2 | 11/2004 | Schwartz et al. | |
| 6,892,091 B1 | 5/2005 | Ben-Haim et al. | |
| 7,756,576 B2 * | 7/2010 | Levin | 600/547 |
| 2003/0078509 A1 | 4/2003 | Panescu | |
| 2006/0173251 A1 | 8/2006 | Govari et al. | |
| 2006/0241401 A1 | 10/2006 | Govari et al. | |
| 2007/0038078 A1 | 2/2007 | Osadchy | |

FOREIGN PATENT DOCUMENTS

| | | |
|---|---|---|
| EP | 1 743 573 B1 | 1/2007 |
| EP | 1 743 575 B1 | 1/2007 |
| WO | 98/48722 A1 | 11/1998 |

OTHER PUBLICATIONS

EP Partial Search Report No. EP 09 25 2596 dated Jan. 12, 2010.

* cited by examiner

*Primary Examiner* — Amy He
(74) *Attorney, Agent, or Firm* — William A. Schoneman

(57) ABSTRACT

Methods and systems method for sensing a position of an object in a body include positioning a probe in the body, making measurements of mapping electrical currents passing between at least a first electrode on the probe and a plurality of second electrodes on a surface of the body, calibrating the measurements so as to compensate for one or more non-ideal features of the measurements including effects of system-dependent electrical coupling to one or more devices other than the first electrode and the second electrodes, and computing the position of the probe in the body using the calibrated measurements.

22 Claims, 4 Drawing Sheets

CALIBRATION AND COMPENSATION FOR ERRORS IN POSITION MEASUREMENT

CROSS-REFERENCE TO RELATED APPLICATIONS

This Application claims the benefit of U.S. Provisional Application No. 61/113,722, filed Nov. 12, 2008, which is herein incorporated by reference.

BACKGROUND OF THE INVENTION

1. Field of the Invention

This invention relates to sensing of electrical signals within a living body. More particularly, this invention relates to sensing of electrical signals, while tracking an object in the body using impedance measurements.

2. Description of the Related Art

A wide range of medical procedures involve placing objects, such as sensors, tubes, catheters, dispensing devices, and implants, within the body. Position sensing systems have been developed for tracking such objects. For example, U.S. Pat. No. 5,983,126, to Wittkampf, whose disclosure is incorporated herein by reference, describes a system in which catheter position is detected using electrical impedance methods. U.S. Patent Application Publications 2006/0173251, to Govari et al., and 2007/0038078, to Osadchy, which are herein incorporated by reference, describe impedance-based methods for sensing the position of a probe by passing electrical currents through the body between an electrode on the probe and a plurality of locations on a surface of the body.

SUMMARY OF THE INVENTION

Impedance-based position measurements typically assume a certain ideal model of current flow and impedance among the elements of the position sensing system. In practice, however, the measurements are affected by non-ideal conditions, such as varying impedance and current leakage through other conductive components that are connected to the patient's body. Embodiments of the present invention, as described hereinbelow, provide methods and systems for calibrating and compensating for the real, non-ideal measurement conditions in which the position sensing system must actually operate.

An embodiment of the invention provides a method for sensing a position of an object in a body, which is carried out by positioning the object in the body, making measurements of mapping electrical currents passing between at least a first electrode on the object and a plurality of second electrodes on a surface of the body, calibrating the measurements so as to compensate for one or more non-ideal features of the measurements including effects of system-dependent electrical coupling to one or more medical devices other than the first electrode and the second electrodes, and computing the position of the object in the body using the calibrated measurements.

According an aspect of the method, calibrating the measurements includes calculating the effects of system-dependent electrical coupling, and calculating mapping generator-induced crosstalk.

In one aspect of the method, calculating the effects of system-dependent electrical coupling is performed prior to positioning the object in the body, and includes providing respective patch measurement circuits to determine respective portions of the mapping electrical currents passing through the second electrodes, electrically bypassing the patch measurement circuits, and thereafter determining respective crosstalk signals experienced by the second electrodes using the patch measurement circuits.

According to another aspect of the method, determining respective crosstalk signals includes determining for each of the second electrodes phases between currents and voltages experienced therein, wherein the currents and voltages are coupled from transmitters connected to the at least one first electrode, respectively.

According to an additional aspect of the method, the one or more medical devices comprise an ablator linked to the object, and a third electrode on the surface of the body, wherein calibrating the measurements includes measuring leakage current flowing in a path extending from the at least one first electrode through the ablator and the third electrode to the second electrodes on the body surface, rather than directly from the at least one first electrode to the second electrodes as desired, and wherein computing the position is performed while the ablator is connected to the body.

According to one aspect of the method, calibrating the measurements also includes linking the second electrodes to respective body surface receivers and body surface generators, and using the body surface receivers and the body surface generators to determine a patch-to-patch conductance matrix among the second electrodes.

A further aspect of the invention includes disconnecting the ablator from the probe, determining an ablator leakage current passing from a generator of one of the mapping electrical currents through the ablator and the third electrode, and determining respective components of the ablator leakage current at the second electrodes and calculating ratios between the components and the ablator leakage current, respectively.

A further aspect of the method includes applying the patch-to-patch conductance matrix to perform frequency compensation of currents measured by the body surface receivers.

Other embodiments of the invention provide apparatus for carrying out the above-described method.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

System Architecture

Figure 1:
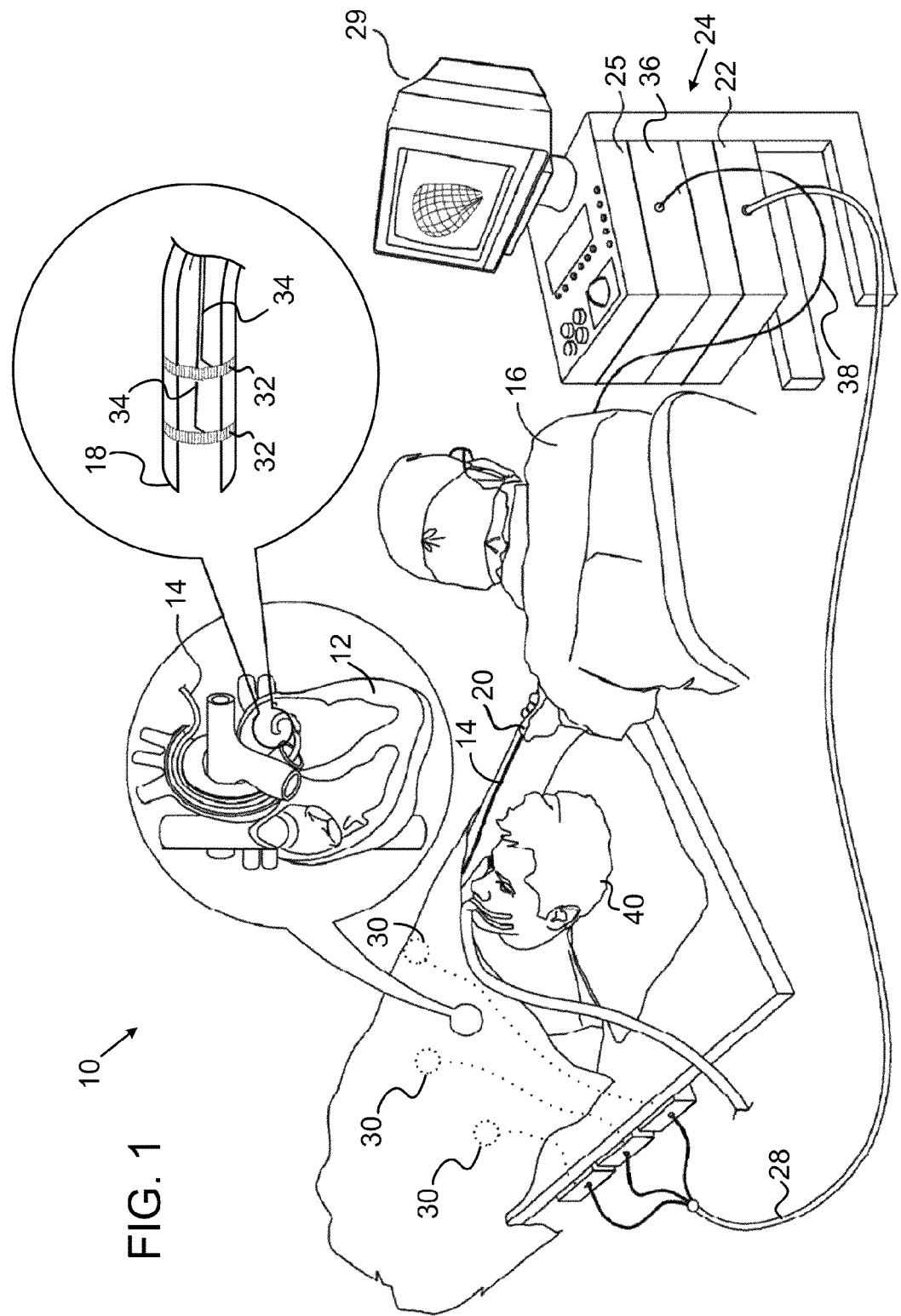
FIG. 1 is a pictorial illustration of a system for detecting areas of abnormal electrical activity and performing ablative procedures on a heart of a living subject, which is constructed and operative in accordance with a disclosed embodiment of the invention.

Turning now to the drawings, reference is initially made to FIG. 1, which is a pictorial illustration of a system 10 for detecting areas of abnormal electrical activity and performing ablative procedures on a heart 12 of a living subject 40 in accordance with a disclosed embodiment of the invention. A probe or catheter 14 having a tip 18 is a component of the system 10, and is percutaneously inserted by an operator 16 through the patient's vascular system into a chamber or vascular structure of the heart. The operator 16 brings a distal portion of the catheter 14 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892,091, whose disclosures are herein incorporated by reference.

Electrical signals can be conveyed from the heart 12 through one or more electrodes 32 located at or near the distal tip 18 of the catheter 14 and through wires 34 to a console 24. Pacing signals and other control signals may be conveyed from the console 24 through the wires 34 and the electrodes 32 to the heart 12. The electrodes 32 also function as components of an impedance-based positioning system for locating the catheter, which is described below. Wire connections 28 link the console 24 with body surface electrodes 30.

Additionally, areas determined to be abnormal by evaluation of the electrical activation maps can be ablated by application of thermal energy, e.g., by passage of radiofrequency electrical current through wires 34 in the catheter to the electrodes 32, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers, to mapping in sinus rhythm, and when many different cardiac arrhythmias are present.

The catheter 14 typically comprises a handle 20, having suitable controls to enable the operator 16 to steer, position and orient the distal end of the catheter as desired for the ablation. A positioning processor 22 calculates location and orientation coordinates of the catheter 14.

The console 24 contains a generator 25, the output of which is connected to one or more electrodes 32 on the outer surface of the catheter 14 by wires 34. The electrodes 32 are at least dual-purpose, being employed to transmit first electrical signals to the heart 12 through the body of the subject 40 to body surface electrodes 30, to be ultimately evaluated by the positioning processor 22. In some embodiments, the operator 16 may cause second electrical signals, containing ablative radiofrequency energy to be conducted to the electrodes 32 from an ablation power generator 36, which can be incorporated in the console 24. Such techniques are disclosed in commonly assigned U.S. Pat. No. 6,814,733, which is herein incorporated by reference.

As noted above, the catheter 14 is coupled to the console 24, which enables the operator 16 to observe and regulate the functions of the catheter 14. The positioning processor 22 is preferably a computer with appropriate signal processing circuitry. The processor is coupled to drive a display monitor 29. The signal processing circuits, typically including an electrocardiographic device 38, receive, amplify, filter and digitize signals from the catheter 14, including signals conveyed via the electrodes 32. The digitized signals are received and analyzed in the console 24 to derive electrical information of medical interest. The information derived from this analysis is used to generate an electrophysiological map of at least a portion of the heart 12 or related structures such as the pulmonary venous ostia. The map may be employed for diagnostic purposes, such as locating an arrhythmogenic area in the heart, or to facilitate therapeutic ablation.

Other signals used by the positioning processor 22 are transmitted from the console 24 through the wires 34 and the electrodes 32 in order to compute the position and orientation of the catheter 14.

The electrocardiographic device 38 may provide an ECG synchronization signal to the console 24, which may be displayed on the display monitor 29 or on a separate display (not shown). The system 10 typically also includes a reference position sensor, either on an externally-applied reference electrode attached to the exterior of the subject's body, or on another internally-placed reference catheter (not shown), which is inserted into the heart 12 and maintained in a fixed position relative to the heart 12. By comparing the position of the catheter 14 to that of the reference catheter, the coordinates of catheter 14 are accurately determined relative to the heart 12, irrespective of heart motion. Alternatively, any other suitable method may be used to compensate for heart motion.

Figure 2:
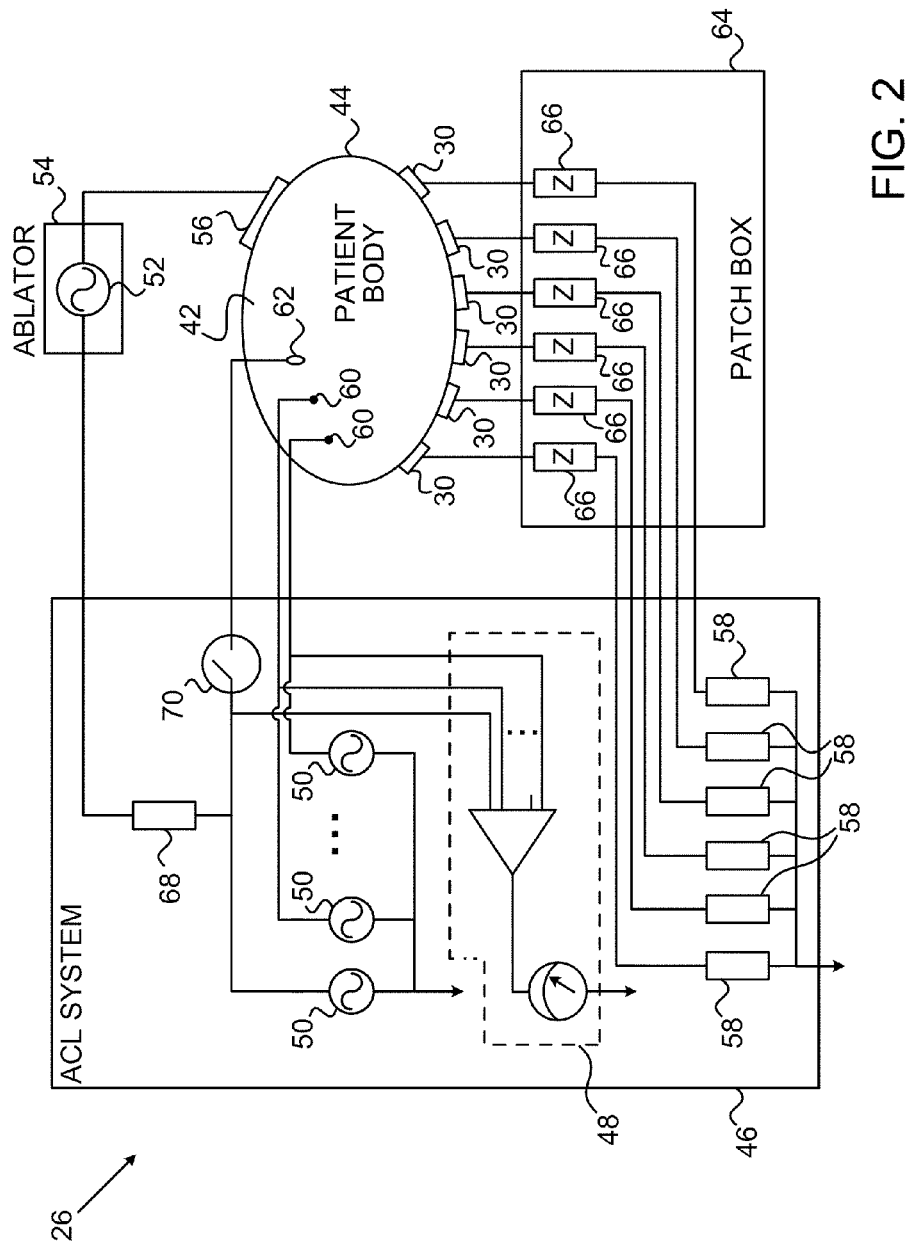
FIG. 2 is a schematic illustration of an impedance-based positioning sub-system of the system shown in FIG. 1, which is constructed and operative in accordance with a disclosed embodiment of the invention.

Reference is now made to FIG. 2, which is a schematic illustration of an impedance-based positioning system 26, which is a component of the system 10 (FIG. 1), shown connected to a patient body 42, in accordance with a disclosed embodiment of the invention. This arrangement is similar to that described in the above-mentioned publications by Osadchy and Govari, modified to operate in accordance with the principles of the present invention. A brief description follows for convenience of presentation:

A plurality of body surface electrodes 30, which can be adhesive skin patches, are coupled to a body surface 44 (e.g., the skin) of the subject. The body surface electrodes 30 are sometimes referred to herein as "patches". In cardiac applications the body surface electrodes 30 are usually distributed so as to surround the heart, three on the chest of the subject and three on the back. However, the number of the body surface electrodes 30 is not critical, and they may be placed at convenient locations on the body surface 44 in the general vicinity of the site of the medical procedure.

A control unit 46, normally disposed in the console 24 (FIG. 1, includes current measurement circuitry 48 and one or more catheter electrode transmitters 50 for driving a current through one or more of the electrodes 32 to one or more of the body surface electrodes 30 at respective working frequencies. The control unit 46 is linked to the positioning processor 22 (FIG. 1). The control unit 46 is linked to an ablator 54, which comprises at least one ablation generator 52. Currents through the body surface electrodes 30 and an ablator body surface electrode 56 flow in a circuit with the ablation generator 52 and are measured by respective current measurement circuits that are disposed within body electrode receivers 58, sometimes referred to herein as "patch measurement circuits". The body electrode receivers 58 are typically incorporated in the control unit 46. Alternatively, they may be affixed to the body surface electrodes 30. Catheter electrodes are represented in FIG. 2 as measurement electrodes 60 (circles) and a dual-purpose electrode 62 (ellipse). The dual-purpose electrode 62 functions as an ablation electrode and also serves as one of the measurement electrodes.

The body surface electrodes 30 are connected to the body electrode receivers 58 via a patch box 64, which protects the system from ablation and defibrillation currents. Typically the system is configured with six body electrode receivers 58. The patch box parasitic impedances 66 (Z), are measured during production and thus known a priori. These impedances are discussed below.

Typically, although only two measurement electrodes 60 are shown for convenience, about 80 measurement electrodes are used for impedance measurements. Typically there are one or two ablation electrodes. The coordinates of a catheter inside the body are determined in the positioning system 26 by passing currents between electrodes on the catheter and the body surface electrodes 30.

The control unit 46 may also control an ablation circuit, comprising ablator 54, and the dual-purpose electrode 62. The ablator 54 is typically disposed externally to the control unit 46 and incorporates the ablation generator 52. It connects with the ablator body surface electrode 56 and to an ablator filter 68, which in this example is shown within the control unit 46. However this location is not essential. A switch 70 configures the ablator circuit for different modes of operation as described below. Voltage measurement circuitry 72 is provided for determining the output of the catheter electrode transmitters 50. It will be noted from inspection of FIG. 2 that the ablation circuit is connected to one of the catheter electrode transmitters 50. The significance of this connection is described below in the section entitled "Ablation Leakage Training Phase".

Figure 3:
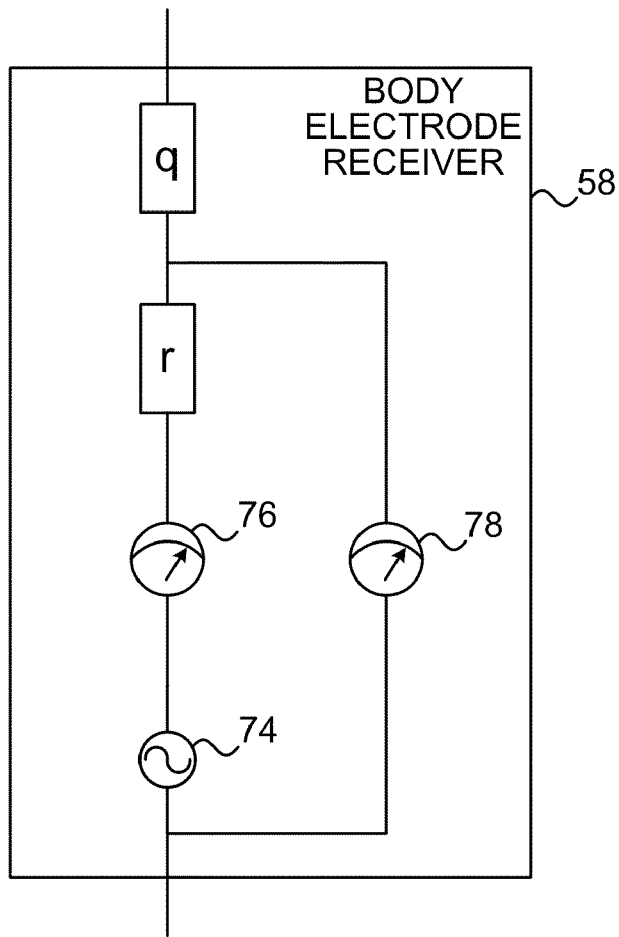
FIG. 3 is an electrical schematic of a body electrode receiver of the sub-system shown in FIG. 2, which is constructed and operative in accordance with a disclosed embodiment of the invention.

Reference is now made to FIG. 3, which is a schematic of an exemplary body electrode receiver 58 (FIG. 2), which is constructed and operative in accordance with a disclosed embodiment of the invention. Ideally, the impedance between the body surface electrodes 30 and ground should be zero. In practice it is not zero and thus it affects the current distribution among the body surface electrodes 30. The effect is frequency dependent and as such, it affects each electrode differently. As will be apparent from the discussion below, during calibration currents of respective frequencies flow through the body surface electrodes 30. This makes it impossible to predict one electrode location based on a mapping performed by another electrode. Another effect that preferably requires compensation is the leakage of positioning current generated by the catheter electrode transmitters 50 (FIG. 2) through the ablation generator 52 and the ablator body surface electrode 56 to the body surface electrodes 30. The objective of the calibration and compensation procedures is to estimate the current that would have flowed if the input impedance of the body surface electrodes 30 were zero and there were no ablator 54 (FIG. 2).

It will be noted that the body electrode receiver 58 includes a body surface electrode generator 74, a current measurement device 76, and a voltage measurement device 78. The body surface electrode generator 74 in different instances of the body electrode receiver 58 may be assigned respective frequencies. Alternatively, the body surface electrode generator 74 may be assigned the same frequency in all instances of the body electrode receiver 58 and they may be time-division multiplexed.

The quantities described with reference to FIG. 3 are as follows:

i—body surface electrode index.

j—Frequency index. This denotes the frequency $f_j$, which is transmitted through body surface electrode j.

$z_{ij}$—The a priori known impedance of the patch box 64 (FIG. 2). This quantity may be fixed during manufacture, or determined in a post-production procedure. In any case it is treated as a known stable quantity.

$q_{ij}$—The a priori known impedance of a component of the transmission path through the body surface electrode that is not included in voltage measurement.

$r_{ij}$—The a priori known impedance of a component of the transmission path through the body surface electrode that is included in voltage measurement.

$E_i$—Voltage source (unknown) that drives the body surface electrode i with frequency $f_i$.

$I_{ij}$—Current measured at body surface electrode i at frequency $f_j$.

$V_{ij}$—Voltage measured at body surface electrode i at frequency $f_j$.

Additional quantities not shown in FIG. 3 are:

$Cv_{ij}$—The a priori known voltage calibration constants; and $Ci_{ij}$—The a priori known current calibration constants.

The quantities $q_{ij}$ and $r_{ij}$ are also referred to as "body surface receiver parasitic impedances".

Figure 4:
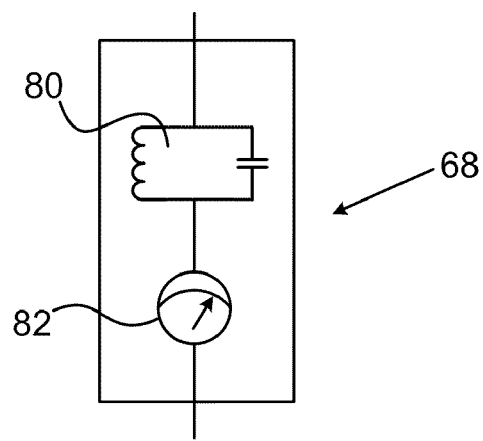
FIG. 4 is an electrical schematic of an ablator filter of the sub-system shown in FIG. 2, which is constructed and operative in accordance with a disclosed embodiment of the invention.

Reference is now made to FIG. 4, which is an electrical schematic of the ablator filter 68 (FIG. 2), showing a notch filter 80 and a current measurement element 82. In normal operation, the notch filter 80 stops most of the current transmitted through the measurement electrodes 60 (FIG. 2), from leaking through the ablator 54 and the ablator body surface electrode 56. The current measurement element 82 measures the residual leakage current through the ablator 54. This measurement is used for ablator leakage compensation during normal operation.

Crosstalk Calibration

Figure 5:
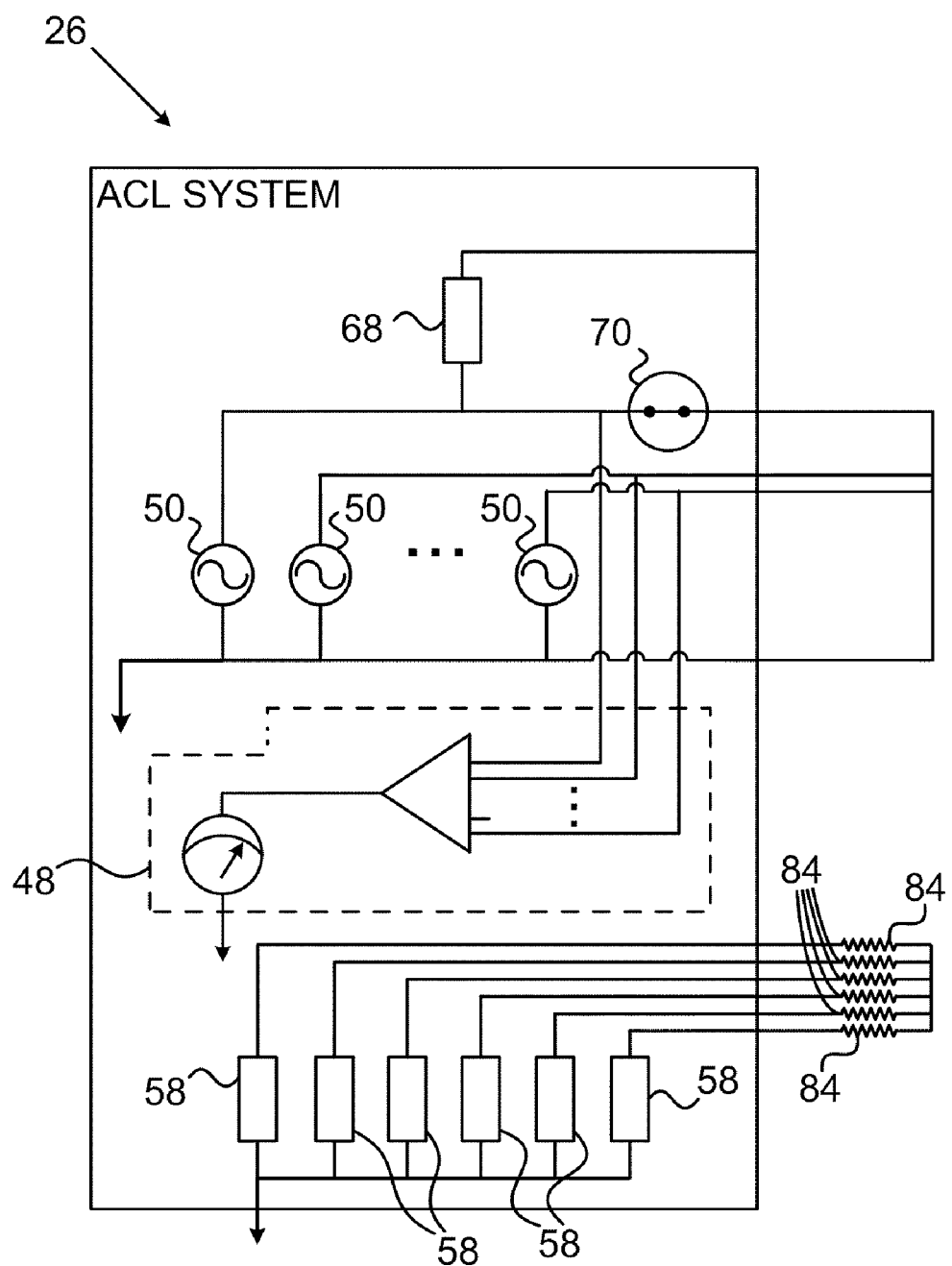
FIG. 5 is a schematic diagram of the positioning subsystem shown in FIG. 2, which is configured for crosstalk calibration, in accordance with a disclosed embodiment of the invention.

Reference is now made to FIG. 5, which is a schematic circuit diagram of the positioning system 26 (FIG. 2), which is configured for crosstalk calibration, in accordance with a disclosed embodiment of the invention. The body electrode receivers 58 are connected to a network of resistors 84 that approximately simulate body impedance. Each of the resistors 84 has a value of about 10 Ohms. The resistive network replaces the connections to the body surface electrodes 30 of normal operation as shown in FIG. 2.

Crosstalk calibration is normally done once, either after completion of manufacture, or during initial field installation. During the crosstalk calibration process, the ablator 54 (FIG. 2) is omitted. The switch 70 is closed. The catheter electrode transmitters 50 are all turned on with their outputs grounded. The voltages of the catheter electrode transmitters 50 are measured simultaneously. The ratios between measured crosstalk current and the transmitter voltages are computed:

$$K_{ij} = \frac{I_{ij}}{V_j},$$

where:

$I_{ij}$—Current measurement at patch i, from electrode j (frequency $f_j$).

$V_j$—Electrode j transmitter measured voltage (frequency $f_j$).

The following calibration data is saved in order to perform crosstalk compensation:

$X_{ij} \equiv Abs(I_{ij})$—Absolute crosstalk value at patch i, from electrode j (frequency $f_j$).

$\phi_{ij}^{X/V} \equiv ARG(K_{ij})$—Phase between current at patch i, from electrode j, and voltage at electrode j.

Training Phase

Reference is again made to FIG. 2. The calculations which follow may be performed by software programs incorporated in the positioning processor 22 (FIG. 1). Additionally or alternatively the calculations may be performed using hardware implementations in the positioning processor 22.

During normal operation, the transmitter voltages and the phase relations between the voltages and total current output are stable. Thus it is possible to perform training infrequently. Alternatively, by training the system as a preliminary to patient procedures, the operator may achieve a higher degree of confidence in the accuracy of the crosstalk compensation.

Referring again to FIG. 1, during the training phase of calibration, at least one of the electrodes 32 should be in the mapping volume, i.e., within a chamber of the heart 12. The positioning system 26 transmits current through this electrode, and the system operates in a first mode, wherein transmitter voltage is measured along with the resulting patch currents. A second (normal) mode of operation, which involves measurements of ablator leakage currents, is described below.

During the training phase the switch 70 (FIG. 2) is closed. The training phase is nearly frequency-independent. Thus it is necessary to perform training with respect to only one of the measurement electrodes 60.

The ratio between the transmitter voltage and the sum of the patch currents is averaged over 5 seconds. We then calculate the phase between the transmitter voltage and total current (sum of patch currents):

$$\phi^{V/I} = Arg\left(\frac{V^e}{\sum_i I_i^e}\right),$$

where:
  e—Is the transmitting electrode.
  $V^e$—Is the measured transmitter voltage.
  $I_i^e$—Current measurement at patch i, from the transmitting electrode.

The use of these measurements is described below.

Online Operation

During normal system operation, the crosstalk current is calculated for every transmitting electrode as follows:

$$I_{ij}^X = X_{ij} \cdot Exp\left\{i\left(\phi_{ij}^{X/V} + \phi^{V/I} + Arg\left(\sum_i I_{ij}\right)\right)\right\}$$

where:
  $X_{ij}$, $\phi_{ij}^{X/V}$—crosstalk calibration constants (as defined above).

$\phi^{V/I}$—Phase between electrode transmitters and currents (see below).

$I_{ij}$—Current measured at patch i at frequency $f_j$.

The compensation is done by subtracting the estimated crosstalk current:

$$Q_{ij} = I_{ij} - I_{ij}^X$$

The values $Q_{ij}$ are used in the discussion below.

Body Impedance Estimation

Estimation of the body impedance matrix is essential for ablator leakage compensation and frequency compensation, as described below.

The measurements are represented as DFT (Discrete Fourier Transform) results: $Q_{ij}$ (after crosstalk compensation) for $I_{ij}$ measurement and $P_j$ for $V_j$ measurement.

Patch-To-Patch Conductance Matrix Estimation

Denote voltages on the patch as $X_{ij}$ (for patch i and frequency $f_j$). Also represent s respective body surface electrode generator 74, which is incorporated in the body electrode receiver 58 (FIG. 2) as multi-frequency $E_{ij} \equiv \delta_{ij} E_j$ (which actually means that patch i transmits only frequency $f_j$). Then:

$$V_{ij} = E_{ij} + r_{ij} I_{ij}$$

$$P_j \equiv \sum_i \frac{V_{ij}}{C v_{ij}} = \sum_i \frac{\delta_{ij} E_j + r_{ij} I_{ij}}{C v_{ij}} = \frac{E_j}{C v_{jj}} + \sum_i \frac{r_{ij} I_{ij}}{C v_{ij}}$$

It follows that:

$$E_j = \left(P_j - \sum_i \frac{r_{ij} I_{ij}}{C v_{ij}}\right) C v_{jj}$$

The voltages on the patches can now be estimated as:

$$X_{ij} = E_{ij} + (r_{ij} + q_{ij} + z_{ij}) I_{ij}$$
$$= \delta_{ij} E_j + (r_{ij} + q_{ij} + z_{ij})$$
$$= \delta_{ij}\left(P_j - \sum_k \frac{r_{kj} I_{kj}}{C v_{kj}}\right) C v_{jj} + (r_{ij} + q_{ij} + z_{ij}) I_{ij}$$

The value of $I_{ij}$ can be calculated from the measurement $Q_{ij}$ by:

$$I_{ij} = Ci_{ij} \cdot Q_{ij}$$

The patch voltages can be calculated now:

$$X_{ij} = \delta_{ij}\left(P_j - \sum_k \frac{r_{kj} Ci_{kj} Q_{kj}}{C v_{kj}}\right) C v_{jj} + (r_{ij} + q_{ij} + z_{ij}) Ci_{ij} Q_{ij}$$

The patch currents and voltages are related via the patient body impedance matrix (which does not depend on frequency):

$$-I_{ij} = \sum_k \sigma_{ik} X_{kj}.$$

The minus sign is due to a convention that positive current flow into the body—but measured as current flowing out of the body. In matrix notation: $-I = \sigma \cdot X$. The patient body impedance matrix is estimated by $\sigma = -I \cdot X^{-1}$. Here, I represents the current matrix, and not the identity matrix:

$$\sigma = -[C_{ij} \cdot Q_{ij}] \cdot [X_{ij}]^{-1}$$

Some additional corrections to $\sigma$ follow, in which there is a transposition of $\sigma$ at the end:

$$S_j \equiv \sum_i \sigma_{ij}$$

$$T \equiv \sum_j S_j$$

$$\sigma_{ij} \leftarrow \sigma_{ji} - \frac{S_i S_j}{T}$$

Ablator Patch Compensation

In this section all the currents are "true measured currents", which means that the patch current DFT values are multiplied by the corresponding calibration constant $Ci_{p,f_j}$, and the ablator leakage current DFT values are multiplied by the corresponding calibration constant $Ci_{f_j}^{abl}$.

Referring again to FIG. 2, the ablator 54 connects to the patient and the positioning system 26. The switch 70 is closed. An ablator electrode is typically located at the tip 18 (FIG. 1) of the catheter 14 and corresponds to dual-purpose electrode 62. Not all of the current that is driven into the dual-purpose electrode 62 flows through the patient body 42 into body surface electrodes 30. Part of the current produced by the catheter electrode transmitters 50 also goes into the ablator 54, entering the patient body 42 through the ablator body surface electrode 56, and finally flows into the body surface electrodes 30. The measurement electrodes 60 are affected, too. Components of their currents follow a path leading through the dual-purpose electrode 62, through the ablator input resistance into the ablator 54, the ablator body surface electrode 56 and finally through the body surface electrodes 30.

Ablation Leakage Training Phase

Continuing to refer to FIG. 2, The ablation leakage training phase of the positioning system 26 begins once the body surface electrodes 30 and the ablator body surface electrode 56 are in place.

During ablation leakage training, the switch 70 is open, so that all the current that would otherwise be driven through the dual-purpose electrode 62 by the corresponding catheter electrode transmitter 50 is forced to flow through the ablator 54 via the ablator body surface electrode 56 to the body surface electrodes 30. The currents through the body surface electrodes 30 $I_{p,f_{M1}}^{abl} \equiv \vec{I}_{f_{M1}}^{abl}$ (p is patch index; $f_{M1}$ is M1 (ablation electrode) frequency) are measured together with the total current through the ablator body surface electrode 56, $I_{f_{M1}}^{8}$. The sum of these currents should be equal to the output of the ablation generator 52 within 20%:

$$\sum_p I_{p,f_{M1}}^{abl} \approx I_{f_{M1}}^{8}$$

The frequency-compensated current is calculated:

$$\vec{I}_{f_{M1}}^{cal} = (I + \sigma \cdot R_{f_{M1}}) \vec{I}_{f_{M1}}^{abl}$$

Now we can calculate the currents $\vec{I}_{f_k}^{abl}$ for every working frequency by using the estimation of the patch-to-patch conductance matrix $\sigma$ as described above:

$$\vec{I}_{f_k}^{abl} = (I + \sigma \cdot R_{f_k})^{-1} \vec{I}_{f_{M1}}^{cal}$$

I—Identity matrix.
$\sigma$—Patch to patch conductance matrix estimated as explained above.
$R_{f_k}$—Diagonal matrix with $(r_{ik} + q_{ik} + z_{ik})$ as the $i^{th}$ diagonal element (the catheter transmits frequency $f_k$).

The ablation current ratios at every frequency are then calculated as:

$$\alpha_{p,f_k} = \frac{I_{p,f_k}^{abl}}{\sum_k I_{k,f_k}^{abl}},$$

where $I_{p,f_k}^{abl}$ is the p component of the vector $\vec{I}_{f_k}^{abl}$. The parameters $\alpha_{p,f_k}$ should be averaged over a predefined time (30 seconds).

Normal Operation

Continuing to refer to FIG. 2, during normal system operation, the switch 70 is closed, and it is assumed that the ablator 54 may be operating at any time thereafter. The currents through the body surface electrodes 30 $I_{p,f_k}$ are measured together with the current through the ablator body surface electrode 56 $I_{f_k}^{8}$. Using the parameters $\alpha_{p,f_k}$ estimated at the initialization phase, the compensation is performed as follows:

$$I_{p,f_k}^{a} = I_{p,f_k} - \alpha_{p,f_k} \cdot I_{f_k}^{8}$$

The resulting compensated currents $I_{p,f_k}^{a} \equiv \vec{I}_{f_k}^{a}$ are transferred forward to a frequency compensation module, which may be implemented as a software routine or a hardware module in the positioning processor 22 (FIG. 1).

Frequency Compensation

We write the body conductance matrix as:

$$\sigma_{body} = \begin{pmatrix} e & s^T \\ s & \sigma \end{pmatrix},$$

where we separate $\sigma_{body}$ into a catheter component and patch component as follows:
e—Total current emitted from the catheter electrode (if excited by a 1V source)
S—Vector of currents received at the patches from the electrode
$\sigma$—The patch to patch conductance matrix, as estimated above.

Let the matrix $\tilde{R}_{f_k}$ represent the electrode and patch resistances at frequency $f_k$ ($\tilde{R}_{f_k}$ is a diagonal matrix with the electrode and patch resistances at the diagonal). We will separate $\tilde{R}_{f_k}$ into catheter (no resistance) and patch parts, $$\tilde{R}_{f_k} = \begin{pmatrix} 0 & 0 \\ 0 & R_{f_k} \end{pmatrix},$$

where $R_{f_k}$ is a diagonal matrix, with $(z_{ik}+q_{ik}+r_{ik})$ as the diagonal element number i.

The complete conductance matrix (body+patch resistances) is given by $$\tilde{\sigma}_{body} = (I + \sigma_{body}\tilde{R}_{f_k})^{-1}\sigma_{body}$$

Making the electrode and patches separation again we get:

$$\tilde{\sigma}_{body} = \begin{pmatrix} \sim & \sim \\ \tilde{s} & \sim \end{pmatrix} = \left( \begin{pmatrix} 1 & 0 \\ 0 & I \end{pmatrix} + \begin{pmatrix} e & s^T \\ s & \sigma \end{pmatrix}\begin{pmatrix} 0 & 0 \\ 0 & R_{f_k} \end{pmatrix} \right)^{-1} \begin{pmatrix} e & s^T \\ s & \sigma \end{pmatrix} =$$

$$\begin{pmatrix} 1 & s^T R_{f_k} \\ 0 & I + \sigma R_{f_k} \end{pmatrix}^{-1} \begin{pmatrix} e & s^T \\ s & \sigma \end{pmatrix} = \begin{pmatrix} \sim & \sim \\ (I + \sigma R_{f_k})^{-1} s & \sim \end{pmatrix}$$

In the final step only relevant quantities were computed. This means that the ideal measurement (where patch resistances are zero) S can be estimated from the real measurements $\tilde{S}$ by:

$$S = (I + \sigma R_{f_k})\tilde{S}$$

Compensation Computation

Writing the ablation compensated current in place of $\tilde{S}$ we get the frequency-compensated currents as:

$$\vec{I}_{f_k}^c = \text{Abs}((I + \sigma R_{f_k}) \cdot \vec{I}_{f_k}^a).$$

Here we convert complex values to real by taking their absolute values.
I—Identity matrix.
σ—Patch to patch conductance matrix estimated above.
$R_{f_k}$—Diagonal matrix with $(r_{ik}+q_{ik}+z_{ik})$ as the $i^{th}$ diagonal element (the catheter transmits frequency $f_k$).
$\vec{I}_{f_k}^a$—Current after ablation leakage compensation.

The resulting vector $\vec{I}_k^c$ is a compensated, frequency-independent measure that depends only on the electrode position.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

What is claimed is:

1. A method for sensing a position of an object in a body, comprising the steps of:
   positioning a probe in the body;
   making measurements of mapping electrical currents passing between at least one first electrode on the object and a plurality of second electrodes on a surface of the body;
   calibrating the measurements so as to compensate for one or more non-ideal features of the measurements including effects of system-dependent electrical coupling to one or more medical devices other than the first electrode and the second electrodes; and
   computing the position of the probe in the body using the calibrated measurements.

2. The method according to claim 1, wherein calibrating the measurements comprises calculating the effects of system-dependent electrical coupling, and calculating mapping generator-induced crosstalk.

3. The method according to claim 2, wherein calculating the effects of system-dependent electrical coupling is performed prior to positioning the probe in the body, and comprises the steps of:
   providing respective patch measurement circuits to determine respective portions of the mapping electrical currents passing through the second electrodes;
   electrically bypassing the patch measurement circuits using a switch; and
   thereafter determining respective crosstalk signals experienced by the second electrodes using the patch measurement circuits.

4. The method according to claim 3, wherein determining respective crosstalk signals comprises determining for each of the second electrodes phases between currents and voltages experienced therein, the currents and voltages being coupled from transmitters connected respectively to the at least one first electrode.

5. The method according to claim 2, wherein the one or more medical devices comprise an ablator linked to the probe, and a third electrode on the surface of the body, wherein calibrating the measurements comprises calculating respective leakage currents flowing in a path extending from the at least one first electrode through the ablator and the third electrode to the second electrodes, and wherein computing the position is performed while the ablator is linked to the body and to a generator of one of the mapping electrical currents.

6. The method according to claim 5, wherein calculating respective leakage currents comprises:
   disconnecting the ablator from the probe;
   determining an ablator leakage current passing from the generator of one of the mapping electrical currents through the ablator and the third electrode; and
   calculating a relation between the ablator leakage current and the mapping electrical currents at respective working frequencies of the mapping electrical currents.

7. The method according to claim 5, wherein calculating respective leakage currents comprises:
   disconnecting the ablator from the probe;
   determining an ablator leakage current passing from the generator of one of the mapping electrical currents through the ablator and the third electrode; and
   determining respective components of the ablator leakage current at the second electrodes; and
   calculating ratios between the components and the ablator leakage current, respectively.

8. The method according to claim 5, wherein calculating respective leakage currents is performed after positioning the probe in the body, and comprises determining a ratio between each of the mapping electrical currents and a summation of the mapping electrical currents passing through the second electrodes.

9. The method according to claim 8, wherein determining the ratio is performed at respective working frequencies of the mapping electrical currents in the second electrodes, and further comprises extrapolating from a portion of the working frequencies to others of the working frequencies.

10. The method according to claim 1 wherein calibrating the measurements further comprises linking the second electrodes to respective body surface receivers and body surface generators, and using the body surface receivers and the body surface generators to determine a patch-to-patch conductance matrix among the second electrodes.

11. The method according to claim 10, further comprising applying the patch-to-patch conductance matrix to perform frequency compensation of currents measured by the body surface receivers.

12. An apparatus for sensing a position of an object, comprising:
a probe adapted to be inserted into a body of a subject;
at least one first electrode disposed near a distal end of the probe;
a plurality of second electrodes adapted to be coupled at respective locations to a surface of the body;
at least one electrode transmitter connected to the first electrode for passing mapping electrical currents between the first electrode on the probe and the second electrodes on the surface of the body; and
a control unit, adapted for making measurements of the mapping electrical currents, for calibrating the measurements so as to compensate for one or more non-ideal features of the measurements including effects of system-dependent electrical coupling to one or more medical devices other than the first electrode and the second electrodes, and for computing the position of the probe in the body using the calibrated measurements.

13. The apparatus according to claim 12, wherein calibrating the measurements comprises calculating the effects of system-dependent electrical coupling, and calculating mapping generator-induced crosstalk.

14. The apparatus according to claim 13, wherein calculating the effects of system-dependent electrical coupling is performed prior to positioning the probe in the body, and comprises the steps of:
providing respective patch measurement circuits to determine respective portions of the mapping electrical currents passing through the second electrodes;
electrically bypassing the patch measurement circuits using a switch; and
thereafter determining respective crosstalk signals experienced by the second electrodes using the patch measurement circuits.

15. The apparatus according to claim 14, wherein determining respective crosstalk signals comprises determining for each of the second electrodes phases between currents and voltages experienced therein, the currents and voltages being coupled from transmitters connected respectively to the at least one first electrode.

16. The apparatus according to claim 13, further comprising an ablator, and a third electrode on the surface of the body, wherein calibrating the measurements comprises calculating respective leakage currents flowing in a path extending from the at least one first electrode through the ablator and the third electrode to the second electrodes, and wherein computing the position is performed while the ablator is linked to the body and to a generator of one of the mapping electrical currents.

17. The apparatus according to claim 16, wherein calculating respective leakage currents comprises:
disconnecting the ablator from the probe;
determining an ablator leakage current passing from the generator of one of the mapping electrical currents through the ablator and the third electrode; and
calculating a relation between the ablator leakage current and the mapping electrical currents at respective working frequencies of the mapping electrical currents.

18. The apparatus according to claim 16, wherein calculating respective leakage currents comprises:
disconnecting the ablator from the probe;
determining an ablator leakage current passing from the generator of one of the mapping electrical currents through the ablator and the third electrode; and
determining respective components of the ablator leakage current at the second electrodes; and
calculating ratios between the components and the ablator leakage current, respectively.

19. The apparatus according to claim 16, wherein calculating respective leakage currents is performed after positioning the probe in the body, and comprises determining a ratio between each of the mapping electrical currents and a summation of the mapping electrical currents passing through the second electrodes.

20. The apparatus according to claim 19, wherein determining the ratio is performed at respective working frequencies of the mapping electrical currents in the second electrodes, and further comprises extrapolating from a portion of the working frequencies to others of the working frequencies.

21. The apparatus according to claim 12 wherein calibrating the measurements further comprises linking the second electrodes to respective body surface receivers and body surface generators, and using the body surface receivers and the body surface generators to determine a patch-to-patch conductance matrix among the second electrodes.

22. The apparatus according to claim 21, further wherein the control unit is operative for applying the patch-to-patch conductance matrix to perform frequency compensation of currents measured by the body surface receivers.

* * * * *